United States Patent [19]

Nason

[11] Patent Number: 4,707,450

[45] Date of Patent: Nov. 17, 1987

[54] SPECIMEN COLLECTION AND TEST UNIT

[76] Inventor: Frederic L. Nason, 6830 Orion Ave., Van Nuys, Calif. 91406

[21] Appl. No.: 912,081

[22] Filed: Sep. 25, 1986

[51] Int. Cl.[4] ............................................. C12M 1/30
[52] U.S. Cl. ................................. 435/295; 435/810; 422/61; 422/102; 128/759; 604/3; 206/438
[58] Field of Search ............... 128/759; 435/292, 294, 435/295, 810; 604/1, 2, 3; 422/58, 59, 61, 99, 101, 102; 206/205, 207, 219, 569, 363, 438

[56] References Cited

U.S. PATENT DOCUMENTS

| | | | |
|---|---|---|---|
| 2,490,168 | 12/1949 | Strauss | 128/759 |
| 3,163,160 | 12/1964 | Cohen | 604/1 X |
| 3,450,129 | 6/1969 | Avery et al. | 128/759 |
| 3,640,268 | 2/1972 | Davis | 128/759 |
| 3,776,220 | 12/1973 | Monaghan | 128/759 |
| 3,792,699 | 2/1974 | Tobin et al. | 435/295 |
| 3,883,396 | 5/1975 | Thomas, Jr. et al. | |
| 3,890,204 | 6/1975 | Avery | 128/759 X |
| 3,890,954 | 6/1975 | Greenspan | 128/759 |
| 3,913,564 | 10/1975 | Freshley | 435/295 |
| 3,915,806 | 10/1975 | Horlach | 435/295 |
| 3,918,435 | 11/1975 | Beall et al. | 604/2 X |
| 3,923,604 | 12/1975 | Monaghan | 206/47 R X |
| 3,954,563 | 5/1976 | Mennen | 435/295 |
| 4,014,746 | 3/1977 | Greenspan | 435/295 X |
| 4,014,748 | 3/1977 | Spinner et al. | 435/295 |
| 4,148,950 | 4/1979 | Brindell et al. | 427/421 |
| 4,175,008 | 11/1979 | White | 435/295 |
| 4,184,483 | 1/1980 | Greenspan | 128/759 |
| 4,196,167 | 4/1980 | Olsen | 422/61 |
| 4,223,093 | 9/1980 | Newman et al. | 435/295 |
| 4,311,792 | 1/1982 | Avery | 128/759 X |
| 4,312,950 | 1/1982 | Snyder et al. | 435/295 |
| 4,340,670 | 7/1982 | Menner | 435/295 X |
| 4,353,868 | 10/1982 | Joslin et al. | 435/295 X |
| 4,387,725 | 6/1983 | Mull | 128/759 |
| 4,409,988 | 10/1983 | Greenspan | 128/759 |
| 4,604,360 | 8/1986 | Hounsell | 435/295 X |

FOREIGN PATENT DOCUMENTS 0155747  9/1985  European Pat. Off. ............ 435/295

*Primary Examiner*—Margaret A. Focarino
*Attorney, Agent, or Firm*—Kelly, Bauersfeld & Lowry

[57] ABSTRACT

A specimen collection and test unit has a fibrous swab tip at one end of an elongated hollow shank for use in collecting a biological specimen. The shank is carried by an elongated base of a resilient plastic material and containing one or more reagents which can be pumped through the shank to the swab tip by applying manual pressure to the base. An elongated cap removably fits onto the base over the swab shank and tip, with the cap including an additional reagent and a well into which the additional reagent can be delivered for contacting the swab tip.

11 Claims, 13 Drawing Figures

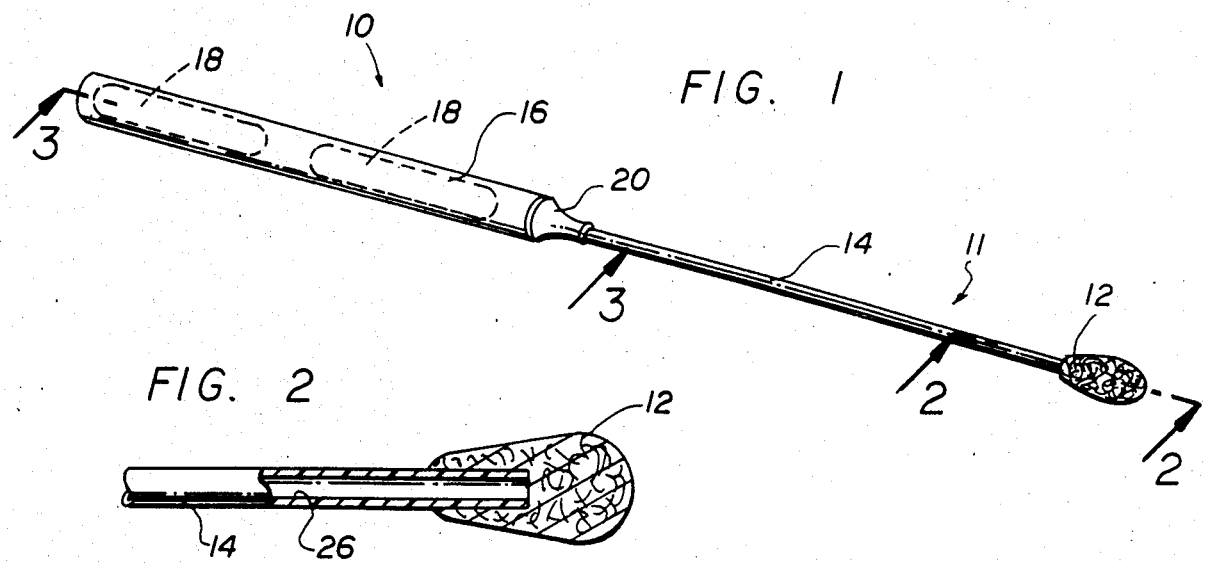
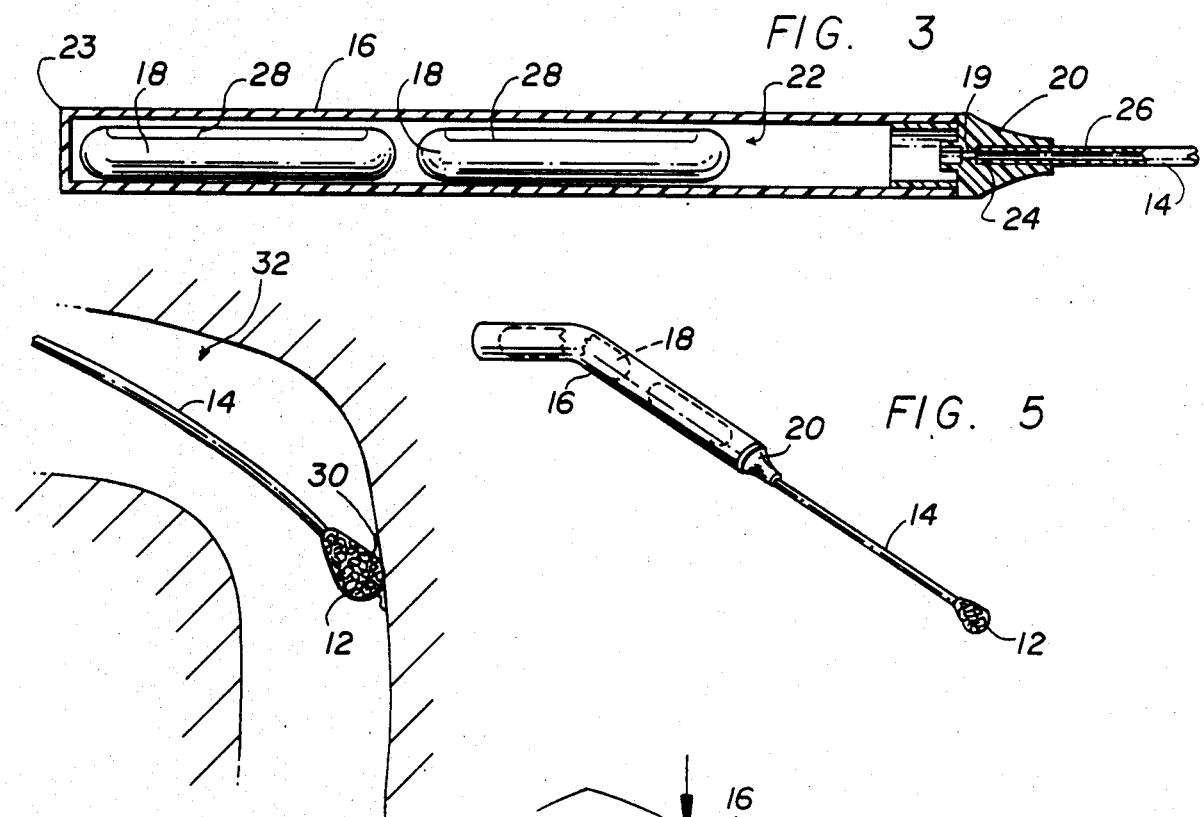

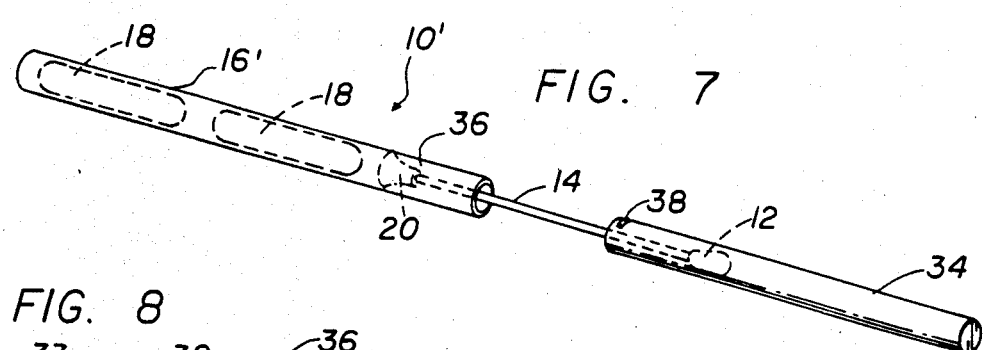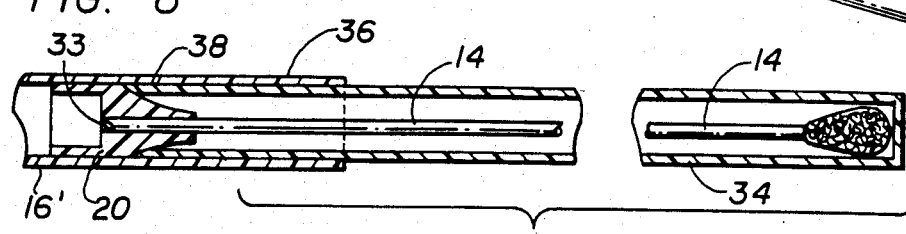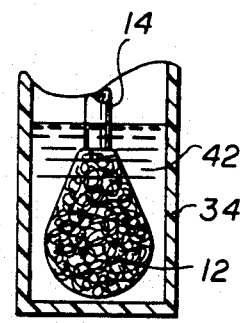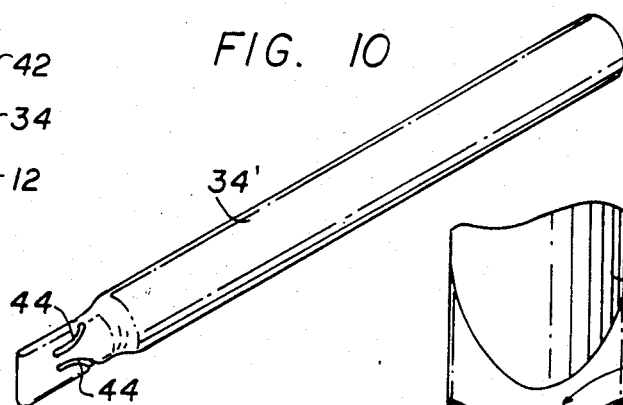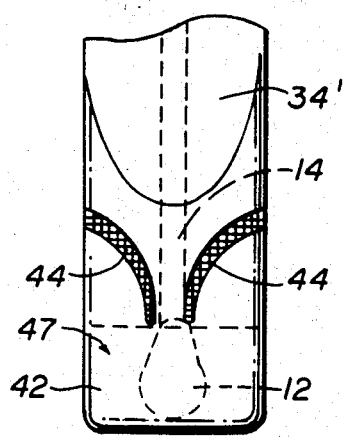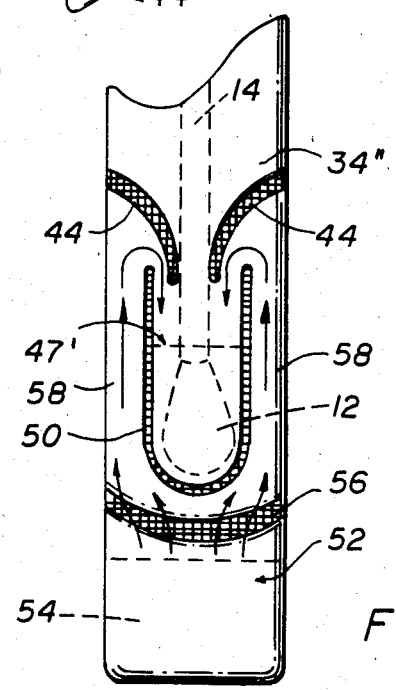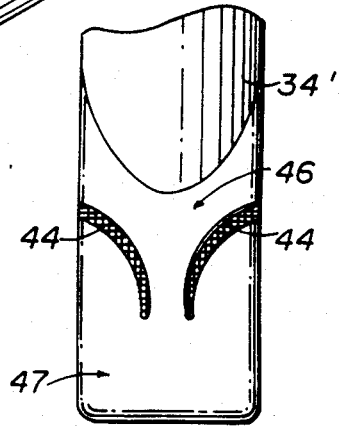

SPECIMEN COLLECTION AND TEST UNIT

BACKGROUND OF THE INVENTION

This invention relates generally to improvements in medical swabs and the like of the type used primarily for collecting biological specimens for purposes of performing a variety of medical tests with respect those specimens. More particularly, this invention relates to a relatively simple and self contained culture collection swab and related apparatus for contacting the swab with one or more selected reagents.

Medical swabs in general are well known in the art for use in collecting biological specimens from a patient for further analysis. Such medical swabs commonly comprise a fibrous swab tip on one end of an elongated stick or shaft which is manually handled to contact the swab tip with selected tissue cells or other biological specimen, for example, within the ear, nose or throat of a patient, resulting in adherence of some of the biological specimen to the swab tip. The thus-collected biological specimen on the swab tip is then contacted with one or more selected reagents which react with the specimen to indicate, for example, the presence of infection or other information regarding patient condition. Tests commonly performed with such collected specimens include, by way of example, fluorescent tests, enzymatic tests, monoclonal based tests, etc.

In accordance with conventional techniques, the collected biological specimen is normally transferred from the swab tip to a laboratory slide or other laboratory apparatus such as a test tube or the like for contact with the selected reagent and further analysis. However, it is frequently difficult to insure transfer of a sufficient specimen quantity from the swab tip to the laboratory slide or the like to insure accurate test results. Moreover, in many instances, the collected specimen must be transported to a medical laboratory or the like for performance of selected assays, but delays between the time of specimen collection and actual test performance can result in partial or complete drying of the specimen, with a corresponding decrease in test reliability.

Various improved swab collection devices have been proposed in efforts to provide enhanced reagent-specimen contact and further to sustain the specimen during post collection transport to a medical laboratory or the like. See, for example, U.S. Pat. No. 3,450,129 which discloses a conventional collection swab removably contained within telescopically interfitting plastic casing components. One of the casing components carries a frangible ampoule with a selected reagent therein, wherein in the ampoule is locked by fiber wadding into one end of the casing component. A biological specimen is collected on the swab tip and the swab is reinserted into the casing, after which the ampoule is broken to permit the reagent therein to soak through the wadding for contacting the adjacent swab tip and collected specimen. However, this device does not insure actual or substantial reagent contact with the biological specimen, nor does it immerse or insure full saturation of the swab tip with the reagent to prevent partial or complete drying of the collected specimen.

The improved specimen collection and test unit of the present invention overcomes these problems and disadvantages by providing an elongated swab for collecting a biological specimen, in combination with means for direct and substantial immersion or saturation contact between the collected specimen and one or more reagents.

SUMMARY OF THE INVENTION

In accordance with the invention, an improved specimen collection and test unit is provided for use in collecting a biological specimen or the like, for example, from a patient. The invention includes relatively simple and self-contained apparatus for applying one or more selected reagents in liquid form directly to the collected specimen, and/or for maintaining the specimen immersed within a liquid reagent. In this manner, selected tests such as medical assays can be performed and/or the collected specimen may be preserved, for example, for transport to and subsequent testing at a medical laboratory or the like.

In accordance with a preferred form of the invention, the specimen collection and test unit comprises an elongated swab having a fibrous tip mounted at one end of an elongated hollow shank. The opposite end of the swab shank is carried by an enlarged, generally cylindrical hollow base formed from a plastic material or the like and having sufficient resiliency to permit manual squeezing and bending without significant plastic deformation. The cylindrical base contains one or more reagents preserved within one or more closed frangible ampoules. When multiple reagents are used, one of the reagents may be provided in nonliquid, preferably powder form.

In use, the swab and base are manually handled as a unit for collecting a biological specimen or the like on the fibrous tip of the swab, without removal of the swab from the cylindrical base. After the specimen is collected, the cylindrical base is manually bent or otherwise deformed to rupture the frangible ampoule or ampoules thereby releasing the reagents therein which can be suitably mixed by gentle shaking of the base. The reagents are thereupon available for pumping through the hollow swab shank to the fibrous tip by application of manual pressure to the cylindrical base. In this manner, the reagents flow into direct and substantial saturating contact with the swab tip and the collected specimen thereon. For many medical assays, reagent contact with the swab tip will produce a colormetric or other visible result thereby permitting direct performance and reading of the test.

In one alternative preferred form of the invention, the cylindrical base is adapted for telescopic interfitting with an elongated cylindrical, cap which defines a removable cover to fit over the swab. The cap is initially removed from the base to permit use of the swab to collect the desired specimen, after which the cap is released, for example, by ampoule breakage and then pumped through the swab shank and the swab tip with the unit oriented in an inverted or cap-down position. The reagent is delivered through the swab tip in sufficient quantity to form a puddle or pool within the cap for direct immersion of the swab tip and collected specimen. In alternative forms, this reagent pool can be associated with seal means for receiving the swab tip and/or means for applying an additional reagent to the swab tip.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings the invention. In such drawings:

FIG. 1 is a perspective view illustrating a specimen collection and test unit embodying the novel features of the invention;

FIG. 2 is an enlarged fragmented sectional view taken generally on line 2—2 of FIG. 1;

FIG. 3 is an enlarged fragmented sectional view taken generally on the line 3—3 of FIG. 1;

FIG. 4 is a somewhat diagrammatic view illustrating use of the invention in the collection of a biological specimen;

FIG. 5 is a perspective view illustrating the step of releasing one or more reagents carried by the test unit;

FIG. 6 is an elevation view depicting reagent transfer to a swab tip for direct contact with a collected biological specimen;

FIG. 7 is an exploded perspective view illustrating an alternative preferred form of the invention;

FIG. 8 is an enlarged fragmented sectional view illustrating contruction details of the test unit of FIG. 7;

FIG. 9 is an enlarged vertical sectional view depicting swab tip immersion in a pool of one or more reagents;

FIG. 10 is a perspective view depicting a modified cap for use with the invention;

FIG. 11 is enlarged fragmented elevation view of a portion of the modified cap shown in FIG. 10;

FIG. 12 is an enlarged fragmented elevation view similar to FIG. 11 but depicting swab tip immersion within one or more reagents; and FIG. 13 is an enlarged fragmented elevation view similar to FIGS. 11 and 12 but illustrating another alternative cap confirguration for use with the invention.

DETAILED DESCRIPTION OF THE PREFERRED EMBODIMENTS

As shown in exemplary drawings, an improved specimen collection and test unit, referred to generally in FIG. 1 by the reference numeral 10 is provided for use in collecting a biological specimen or the like and for performance of a selected test, such as a medical assay, with respect to the collected specimen. The test unit 10 comprises the combination of a swab 11 having a swab tip 12 carried at the forward end of an elongated swab shank 14, with the rear end of the shank 14 being anchored within an enlarged base 16 having one or more reagents 18 therein.

The improved specimen collection and test unit 10 of the present invention advantageously provides a relatively simple and self-contained product for collecting and testing biological specimens such as tissue cells collected from a patient. The test unit provide means for substantial and thorough contact of the collected specimen with one or more selected reagents without requiring additional test apparatus such as laboratory slides, test tubes, and the like. A wide variety of selected tests may be performed and the results read directly at the swab tip 12, after which the entire test unit 10 may be discarded as a disposable item. Alternately, in some forms of the invention, the test unit may include a removable cap (FIGS. 7-13) for insuring complete immersion of the swab tip and collected specimen within a liquid reagent for a selected incubation period and/or during transport of the specimen to a laboratory for further analysis. Examples of tests in which the test unit 10 may be used include, but are not limited to, fluorescent tests, enzymatic tests, monoclonal based tests, etc.

As shown in detail in FIGS. 1-3, the specimen collection and test unit 10 comprises an elongated, relatively thin implement having a size and shape for easy manual handling during use. More specifically, the test unit 10 comprises the swab tip 12 of cotton or Dacron or other absorbent fibrous material wound or otherwise attached in any suitable manner to the forward end of the swab shank 14. This swab shank 14 is provided in the form of a slander hollow tube formed from a relatively stiff but somewhat flexible plastic material or the like adapted for conventional use in the collection of specimens.

The swab shank 14 has its rear end seated against a stop 19 within a matingly shaped fitting 20 which in turn closes the forward end of the enlarged base 16. This base 16 has an elongated, generally cylindrical configuration to provide an effective extension of the swab shank 14 and further to define an internal chamber 22 having its rear end closed by an end wall 23. An open bore 24 is formed through the fitting 20 to provide communication between the base chamber 22 and an interior passage 26 through the swab shank 14, wherein this passage 26 leads without interruption directly to the swab tip 12.

The base 16 contains one or more selected reagents 18, with two of such reagents being shown in the exemplary drawings encapsulated within a pair of frangible ampoules 28 of thin glass or the like. These reagents may be provided in liquid form or, if desired, one of multiple reagents may be provided in powdered or freeze dried form or the like. Alternately, a single reagent within a single ampoule, or more than three reagents within an appropriate number of ampoules may be provided according to the requirements of the particular test to be performed. In any case, the ampoule or ampoules 28 are adapted for breakage by crushing from the exterior of the base 16 by bending or squeezing the base as shown generally in FIG. 5. In this regard, the base 16 is constructed from a somewhat resilient plastic material such as polyethylene or polypropylene or the like adapted for bending or squeezing to crush the ampoules 28 and release the reagents therein without significant plastic deformation of the base.

In use, the test unit 10 is removed from an appropriate package (not shown) which may accommodate sterilization, as required. The unit is then manually handled as illustrated generally in FIG. 4 to collect a biological specimen, for example, such as tissue cells 30 together with micro organisms such as viruses, bacteria, etc, from the throat 32 of a patient. A wide variety of other types of biological specimens may be collected, in accordance with the test or analysis to be performed. Conveniently, the shank 14 has sufficient bending capability as viewed in FIG. 4 to accommodate specimen collection, while also providing sufficient rigidity to permit the swab tip 12 to be pressed or scraped against tissue to collect an adequate specimen.

Once the specimen has been collected on the swab tip 12, the cylindrical base 16 of the test unit is bent or squeezed or otherwise deformed to fracture the ampoule or ampoules 28 thereby releasing the reagents 18 contained therein. When multiple reagents are provided, the released reagents may be mixed within chamber 22 of the base 16 by gentle rocking or swirling motion. Accordingly, the invention permits use of reagents which otherwise exhibit short or unstable shelf lives after mixing, since reagent mixing can be postponed until test performance is desired. The released reagents within the base chamber 22 are then pumped through the swab shank passage 26 by application of gentle manual pressure to the base 16, as viewed in FIG. 6. This permits the reagents to be supplied through the swab shank in sufficient quantity to fully saturate the swab tip 12, thereby insuring substantially complete contact with the collected specimen for accurate test results.

For many types of tests, the results can be read directly upon or a few minutes after the reagent contact with the collected specimen on the swab tip 12. For example, colormetric tests will yield the desired color change directly at the swab tip, without requiring specimen transfers to a laboratory slide or the like for further analysis. When the test is read, the entire collection and test unit 10 may be conveniently discarded.

In one alternative form of the invention as viewed in FIGS. 7-9, the collection and test unit includes a modified hollow base 16' adapted for telescopic interfitting with a removable cap 34. The cap 34 can be used to retain an excess quantity of reagents in a pool for direct immersion by the swab tip 12 and collected specimen thereon. In this version, the test unit may be used in tests requiring relatively longer specimen-reagent incubation periods and/or as a transport device for specimen transport to a laboratory facility or the like for further testing.

More particularly, as shown in FIGS. 7 and 8, a modified test unit 10' corresponds with the test unit 10 previously described with respective FIGS. 1-6, except that the base 16 includes a forward sleeve extension 36 protruding beyond the shank fitting 20 in concentric spaced relation about a rearward portion of the swab shank 14. This extension sleeve 36 is sized and shaped for telescopic reception of the open end of the otherwise closed cylindrical cap 34 which has a size and shape to fit over the swab tip 12 and shank 14 in seated relation within the extension 36. In this embodiment, the rear end of the swab shank 14 is sharply angled as viewed in FIG. 8 and normally positioned in front of a membrane 33 sealing the base chamber. Lock means such as the illustrative tab 38 on the cap 34 may be provided to seat within an indent within the sleeve extension 36 (FIG. 8) to releasably lock the components together in a closed package which may be presterilized.

In use, the cap 34 is removed from the swab to permit collection of a biological specimen or the like in the same manner described previously with respect to FIGS. 1-6. Subsequent to specimen collection, the cap 34 is returned to seated relation within the base sleeve 36, thereby enclosing the swab shank 14 and tip 12. The base 16 can then be deformed appropriately to crush the reagent ampoules 18 therein. The reagent or reagents are then released for passage through the swab shank by pushing the shank firmly into the cap 34 thereby piercing the membrane 33 with the rear end of the shank. This establishes communication between the base chamber and the swab shank to permit delivery of the reagents through the swab shank to saturate the swab tip 12. However, in this embodiment, an excess quantity of the reagent is delivered to and through the swab tip 12 thereby creating a reagent pool or puddle 42 which will be contained in and about the swab tip when the test unit 10' is maintained in an inverted, cap-down position as viewed in FIG. 9. Accordingly, the specimen on the swab tip 12 can be immersed directly into the reagents for a prolonged or extended time period as required, for example, with some tests to be performed. Alternately, the package can be transported in the inverted position to a laboratory or the like for further testing, with the reagent pool 42 preventing undesired drying and corresponding deterioration of the specimen. At the laboratory, the reagent pool 42 which contains the specimen due to reagent flow through the swab tip can be poured from the cap for analysis, or the specimen/reagent pool can be drawn upwardly into the tip and shank for dispensing onto a slide or the like, by appropriate manual squeezing and release of the base 16'. Still further, in alternative uses, the reagents can be delivered to or through the tip to contact the specimen prior to redraw of the reagents and specimen into the swab shank, if desired.

FIGS. 10-12 illustrate a modified geometry for a cylindrical cap for use with the test unit 10' of FIGS. 7-9. More particularly, an alternative cylindrical cap 34' of plastic or the like can be provided with its closed end deformed as by heat staking or the like to a roughly flattened geometry defined by a pair of arcuate stakes 44 interconnecting opposed walls of the cap. These stakes 44 define a smoothly curved, converging entrance opening 46 for receiving the swab tip 12 into a reagent well 47 at the end of the cap 34'. Importantly, the spacing between the stakes 44 in chosen for resilient passage of the swab tip 12 and then to effectively seal against the shank 14, as viewed in FIG. 12.

Accordingly, subsequent to specimen collection, the modified cap 34' is replaced onto the unit base 16' (FIG. 7), resulting in the swab tip 12 passing beyond the stakes 44 and into the substantially closed reagent well 47. Delivery of reagents through the hollow swab shank 14 to the tip 12, as previously described, thus delivers the reagents directly into the well 47 where they are substantially sealed against leakage therefrom by the engagement of the heat stakes 44 with the shank 14. Accordingly, this package design insures the presence of the reagent pool 42 with the swab tip immersed directly into the reagents for a prolonged or extended time period as required, for example, with some tests to be performed. Alternately, the package can be transported to a laboratory or the like for further testing, with the reagent pool 42 preventing undesired drying of the specimen irrespective of the orientation of the unit during transport.

FIG. 13 depicts another modified geometry for a cylindrical cap for use with the test unit 10'. In this embodiment, a cap 34" further includes means for applying an additional reagent to the specimen collected on a swab tip 12. More specifically, the modified cap 34" shown in FIG. 13 includes a pair of contoured heat stakes 44 defining a converging entrance opening 46 for passage of the swab tip 12 subsequent to specimen collection, and for substantial sealing against the swab shank 14 in the same manner described with respect to FIGS. 10-12. However, in this embodiment, the swab tip is received past the stakes 44 into a reagent well 47' defined by a generally U-shaped stake 50 opening toward the passage 46. Accordingly, reagents delivered through the swab shank 14 to the tip 12 may be collected within the well 47' to immerse the tip 12 within the reagents.

The modified cap 34" further includes a lower reagent chamber 52 at the end of the cap, and within which an additional selected reagent 54 is contained in spaced relation with the well 47' by means of a knurled seal 56. This knurled seal 56 may be formed by sonic sealing or the like to provide a breakable valve or seal through with the additional reagent 54 can be delivered by manually pressing upon the cap at the sides of the chamber 52. This delivers the reagent 54 upwardly past the seal 56 to jettison the reagent through small passages 58 at the sides of the well 47' before turning downwardly by the stakes 44 to enter the well 47'. Accordingly, as required by some tests, the specimen may be allowed to stand in the reagents delivered through the shank 14 for a selected period, followed by subsequent addition of the reagent 54.

The improved specimen collection and test unit of the present invention thus provides a relatively simple yet highly versatile apparatus for applying selected reagents to collected biological specimens. The invention can be used for performing tests directly at the swab tip, or for preparing and/or transport of the collected specimen to a laboratory or the like for subsequent testing. One or more reagents can be provided for premixing before delivery to the specimen, or for sequential delivery, as desired. Moreover, relatively unstable and/or toxic reagents can be used, or reagents otherwise incompatible for use with plastic materials can be used, since the reagents are retained within appropriate storage until immediately prior to use.

A variety of modifications and improvements to the invention described herein are believed to be apparent to those skilled in the art. Accordingly, no limitation on the invention is intended by way of the description, except to set forth the appended claims.

What is claimed is:

1. A specimen collection and test unit comprising:
    a swab including an elongated hollow swab shank having a swab tip at one end thereof for use in collection of a biological speciment or the like;
    a hollow base secured to the opposite end of said swab shank and having at least one reagent therein, said base being formed from a material having sufficient resiliency for manual pressing to pump the reagent within said base through said swab shank to said swab tip for direct contact with the specimen collected on said tip;
    a cap removably mounted on said base and enclosing said swab when mounted on said base, said cap defining an open end for receiving said swab and a closed, opposite end defining a well for retaining at least a portion of the reagent pumped to said swab tip in a position with said swab tip immersed within the reagent;
    seal means on said cap for substantial sealing with said swab shank at a position above the swab tip when said swab is received through the interior of said cap into said well and to prevent leakage of the portion of the reagent from said well; and
    means within said cap for storing an additional reagent and means for selectively delivering said additional reagent to said well.

2. The unit of claim 1 wherein said base has an elongated, generally cylindrical shape having one end thereof connected to said shank.

3. The unit of claim 1 wherein said at least one reagent within said base is contained within a fragible ampoule, said base being sufficiently deformable for crushing said ampoule from the exterior of said base.

4. The unit of claim 3 wherein said at least one reagent comprises a pair of reagents respectively within a pair of fragible ampoules.

5. A specimen collection and test unit, comprising:
    an elongated hollow swab shank having an uninterrupted passage formed therethrough;
    an absorbent swab tip at one end of said shank in direct communication with said passage;
    an elongated base having an internal chamber and connected generally at one end to the opposite end of said swab shank with said chamber in direct communication with said passage, said base being formed from a sufficiently resilient material to permit at least partial collapse upon manual pressing thereof;
    at least one frangible ampoule within said base and containing a liquid reagent, said ampoule being breakable upon deformation of said base to release the reagent therein for delivery upon manual pressing of said base through said passage to said swab tip;
    a cap removably mounted on said base, said cap enclosing said swab when mounted on said base, said cap having an elongated shape defining an open end for receiving said swab and a closed, opposite end defining a wall for retaining a portion of the reagent pumped to said swab tip in a position with said swab tip immersed within the reagent;
    seal means on said cap for substantial sealing with said swab shank at a position above the swab tip when said swab is received through the interior of said cap into said well and to prevent leakage of the portion of the reagent from said well; and
    means within said cap for storing an additional reagent and for selectively delivering said additional reagent to said well.

6. The unit of claim 5 wherein said at least one reagent comprises a plurality of reagents respectively within a plurality of frangible ampoules.

7. A specimen collection and test unit, comprising:
    an elongated hollow swab shank having an uninterrupted passage formed therethrough;
    an absorbent swab tip at one end of said shank in direct communication with said passage;
    an elongated base formed as an elongated, open-ended cylinder having a fitting at the open end thereof for mating reception of the opposite end of said swab shank, said fitting having a bore permitting direct communication between said shank passage and an internal chamber formed within said base;
    at least one frangible ampoule within said base and containing a liquid reagent, said ampoule being breakable upon deformation of said base to release the reagent therein for delivery upon manual pressing of said base through said passage to said swab tip;
    an elongated, open-ended cap for receiving said swab shank and said swab tip, said base and said cap including telescopically interfitting means for cooperatively enclosing said swab shank and said swab tip, said interfitting means comprising an extension sleeve on said base for removably receiving the open end of said cap;
    the end of said cap opposite said open end comprising a closed end defining a well and including means for substantially sealed engagement with said swab shank at a position above the swab tip when said swab tip is received through the interior of said cap into said well; and
    means within said cap for storing an additional reagent within said cap for storing an additional reagent and for selectively delivering said additional reagent to said well.

8. The unit of claim 7 wherein said at least one reagent comprises a pair of reagents respectively within a pair of frangible ampoules.

9. The unit of claim 7 wherein said cap is formed from a deformable plastic material, said means for storing and delivering said additional reagent comprising a seal joining together opposite sides of said cap in spaced relation to said cap closed end, said additional reagent being contained between said seal and said closed end, said opposite sides of said cap being manually depressable to force said additional reagent past said seal to said well.

10. The unit of claim 9 wherein said cap further defines flow channels for communicating said additional reagent forced past said seal to said well.

11. The unit of claim 7 wherein said fitting bore is interrupted by a piercable membrane, said base having a relatively sharp opposite end and being slidable within said fitting for piercing said membrane.

* * * * *